United States Patent [19]
Cemenska et al.

[11] Patent Number: 5,701,863
[45] Date of Patent: Dec. 30, 1997

[54] AQUEOUS FUEL EMULSION IDENTIFICATION SYSTEM AND ANTI-TAMPERING DEVICE FOR AN INTERNAL COMBUSTION ENGINE

[75] Inventors: Richard A. Cemenska, Edelstein; Gerald N. Coleman, Peoria; James E. Sibley, Metamora, all of Ill.

[73] Assignee: Caterpillar Inc., Peoria, Ill.

[21] Appl. No.: 778,928

[22] Filed: Jan. 3, 1997

Related U.S. Application Data

[60] Provisional application No. 60/026,616 Sep. 24, 1996.

[51] Int. Cl.$^6$ ................................ F02B 77/00
[52] U.S. Cl. ........................ 123/198 D; 123/25 C
[58] Field of Search ............... 123/1 A, 25 C, 123/198 D

[56] References Cited

U.S. PATENT DOCUMENTS

| | | | |
|---|---|---|---|
| 4,175,635 | 11/1979 | Thomas | 180/287 |
| 4,378,321 | 3/1983 | Miller | 261/41 D |
| 4,553,127 | 11/1985 | Issa | 340/64 |
| 4,594,968 | 6/1986 | Degobert et al. | 123/1 A |
| 4,706,630 | 11/1987 | Wineland et al. | 123/478 |
| 4,869,219 | 9/1989 | Bremmer et al. | 123/383 |
| 4,909,225 | 3/1990 | Gonze et al. | 123/494 |
| 4,974,552 | 12/1990 | Sickafus | 123/1 A |
| 5,016,180 | 5/1991 | Fujisawa | 364/431.04 |
| 5,138,986 | 8/1992 | Aguilar | 123/179.3 |
| 5,186,149 | 2/1993 | Kitajima et al. | 123/491 |
| 5,233,944 | 8/1993 | Mochizuki | 123/1 A |
| 5,237,978 | 8/1993 | Bailey | 123/515 |
| 5,303,842 | 4/1994 | Harp et al. | 220/562 |
| 5,390,640 | 2/1995 | Saito et al. | 123/491 |

*Primary Examiner*—Noah P. Kamen
*Attorney, Agent, or Firm*—Robert J. Hampsch

[57] ABSTRACT

A system and method for the identification of the fuel being transported within a fuel delivery system of an internal combustion engine that may utilize an advanced fuel such as a fuel in water emulsion is provided. The identification of the fuel is accomplished using a fuel identification sensor that distinguishes the fuel type based on differences in optical properties, electrical properties, physical properties, or other characteristics between an aqueous fuel emulsion and a conventional fuel. The disclosed fuel identification device is readily incorporated in an anti-tampering device for preventing the use of a conventional fuel, such as diesel fuel, in an engine designed and certified for aqueous fuel emulsions.

25 Claims, 5 Drawing Sheets

Fig. 2

AQUEOUS FUEL EMULSION IDENTIFICATION SYSTEM AND ANTI-TAMPERING DEVICE FOR AN INTERNAL COMBUSTION ENGINE

CROSS REFERENCE TO RELATED APPLICATIONS

This application is based, in part, on the material disclosed in United States provisional patent application Ser. No. 60/026,616 filed Sep. 24, 1996.

FIELD OF THE INVENTION

The present invention relates to a fuel identification system for an internal combustion engine, and more particularly, to an anti-tampering device for an internal combustion engine that is adapted to utilize an aqueous fuel emulsion as a source of fuel. Still more particularly, the present invention relates to an anti-tampering method and device for the detection and identification of a transported fuel within a fuel delivery system of an internal combustion engine. If the detected fuel is identified as an improper fuel, the system terminates engine operation.

BACKGROUND

Recent fuel developments have resulted in a number of aqueous fuel emulsions comprised essentially of a carbon based fuel, water, and various additives. These aqueous fuel emulsions may play a key role in finding a cost-effective way for internal combustion engines including, but not limited to, compression ignition engines (i.e. diesel engines) to achieve the reduction in emissions below the mandated levels without significant modifications to the engines, fuel systems, or existing fuel delivery infrastructure.

Advantageously, aqueous fuel emulsions tend to reduce or inhibit the formation of nitrogen oxides (NOx) and particulates (i.e. combination of soot and hydrocarbons) by altering the way the fuel is burned in the engine. Specifically, the fuel emulsions are burned at somewhat lower temperatures than a comparable non-aqueous fuel due to the presence of water. This, coupled with the realization that at higher peak combustion temperatures, more NOx are typically produced in the engine exhaust, one can readily understand the advantage of using aqueous fuel emulsions.

Thus, the reduction in NOx is achieved using aqueous fuels primarily because an aqueous fuel emulsion has a lower peak combustion temperature. The actual reduction achieved, however, depends on a number of factors including the composition of the fuel emulsion (e.g. fuel to water ratio), engine/ignition technology, engine operating conditions, etc. Moreover, having a lower peak combustion temperature does not necessarily mean that the aqueous fuel is providing less total energy or doing less work for a given mass of hydrocarbon fuel. Rather, the addition of water only requires a proportional increase in the volume of aqueous fuel to be injected in order to achieve the equivalent amount of work. However, as the volume of fuel that has to be injected increases, the engine performance considerations change. For example, the additional volume of aqueous fuel required in order to achieve the same amount of work imposes additional constraints and other design considerations in the fuel delivery systems, fuel control systems, fuel storage systems and other related systems in the internal combustion engine. Thus, where aqueous fuel emulsions are used, selected changes to the engine system must be incorporated. However, such changes are beneficial only if the aqueous fuel emulsions are used and are often detrimental to the operation of the engine if more conventional fuels are used.

Another problem with developing compression ignition engines to run on an aqueous fuel emulsion is that if a particular engine rating is developed, certified and sold as an aqueous fuel engine it is still capable of operating on diesel fuel. An engine designed for an aqueous fuel typically produces higher power and significantly higher emissions when a conventional fuel, such as diesel fuel is used. It is anticipated that various regulatory agencies may require anti-tampering devices to ensure that such an engine, certified to run on aqueous fuel emulsions, is not run on a more conventional fuel, such as diesel fuel. In addition, for reliability and warranty related purposes, the engine manufacturer and chassis manufacturer want to ensure that diesel fuel is not used to power an engine designed for an aqueous fuel emulsion. Thus, there is a need for such anti-tampering devices that can identify the fuel being used in an internal combustion engine.

SUMMARY OF THE INVENTION

The present invention addresses the above and other needs by providing a method and system for the detection and identification of the fuel being transported within a fuel delivery system of an internal combustion engine that is adapted to utilize an aqueous fuel emulsion. If the transported fuel is identified as an improper fuel, the fuel control system restricts or otherwise disables the engine operation.

In one embodiment, the invention may be characterized as a fuel identification system incorporating a fuel identification sensor for preventing the use of a selected fuels in an internal combustion engine. The fuel identification sensor is disposed along the fuel line in fluid communication between the fuel tank and the fuel pump or unit injectors. The fuel identification sensor provides an input signal to a control unit that is adapted to differentiate between an aqueous fuel emulsion and more conventional fuels and produce a signal that disables the engine when a fuel other than the aqueous fuel emulsion is being transported within the fuel line and that is to be injected into the cylinders. The fuel identification sensor may take the form of an optical sensor, a conductivity sensor, or similar such device capable of distinguishing an aqueous fuel emulsion from a conventional fuel based on the differences between the two types of fuels. The fuel characteristics that are used to distinguish an aqueous fuel from a more conventional fuel includes such characteristics as optical properties, electrical properties, physical properties, and the like.

The disclosed invention may also be characterized as a anti-tampering device for preventing the use of selected fuels in a diesel engine where the engine is adapted to use an aqueous fuel emulsion. The anti-tampering device includes a fuel identification sensor adapted to detect selected physical characteristics (e.g. optical or electrical properties) of the fuel and a control unit responsive to said fuel identification sensor. The control unit is adapted to differentiate between an aqueous fuel emulsion and conventional diesel fuels and disable the engine when an improper fuel is detected. In addition, the anti-tampering device may optionally include a countercheck detector operatively coupled to the fuel identification sensor or control unit and adapted to indicate whether the fuel identification sensor has been altered or otherwise disabled by the engine operator. For example, a countercheck detector may consist of a fuel flow measurement device operatively coupled to the fuel identification sensor and adapted to indicate whether the fuel flow proximate the fuel identification sensor has been diverted or altered.

Finally, the present invention may also be characterized as a method for preventing the use of selected other fuels in an internal combustion engine adapted to use an aqueous fuel emulsion. The disclosed method includes the steps of: (a) detecting selected fuel characteristics (e.g. optical properties, electrical properties, or physical properties) of a fuel in the fuel delivery system of upstream of the engine; (b) identifying the fuel within the fuel delivery system as either an aqueous fuel emulsion or a fuel other than an aqueous fuel emulsion based on the detected fuel characteristics; and (c) disabling the engine when a fuel other than the aqueous fuel emulsion is identified as being present within the fuel delivery system. Preferably, the engine is disabled by limiting the fuel flow to the engine.

In the disclosed embodiments, the fuel identification is accomplished by using either an optical sensor, conductivity meter, or other sensing device that is adapted to sense physical properties of the fuel in the fuel delivery system. Because selected optical, electrical and physical properties of an aqueous fuel emulsion differ from those of conventional fuels, the use of standard sensing techniques presents a simple yet reliable means for detecting the type of fuel in the fuel delivery system.

BRIEF DESCRIPTION OF THE DRAWINGS

The above and other aspects, features, and advantages of the present invention will be more apparent from the following, more descriptive description thereof, presented in conjunction with the following drawings, wherein.

Corresponding reference numbers indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principals of the invention. The scope and breadth of the invention should be determined with reference to the claims.

Figure 1:
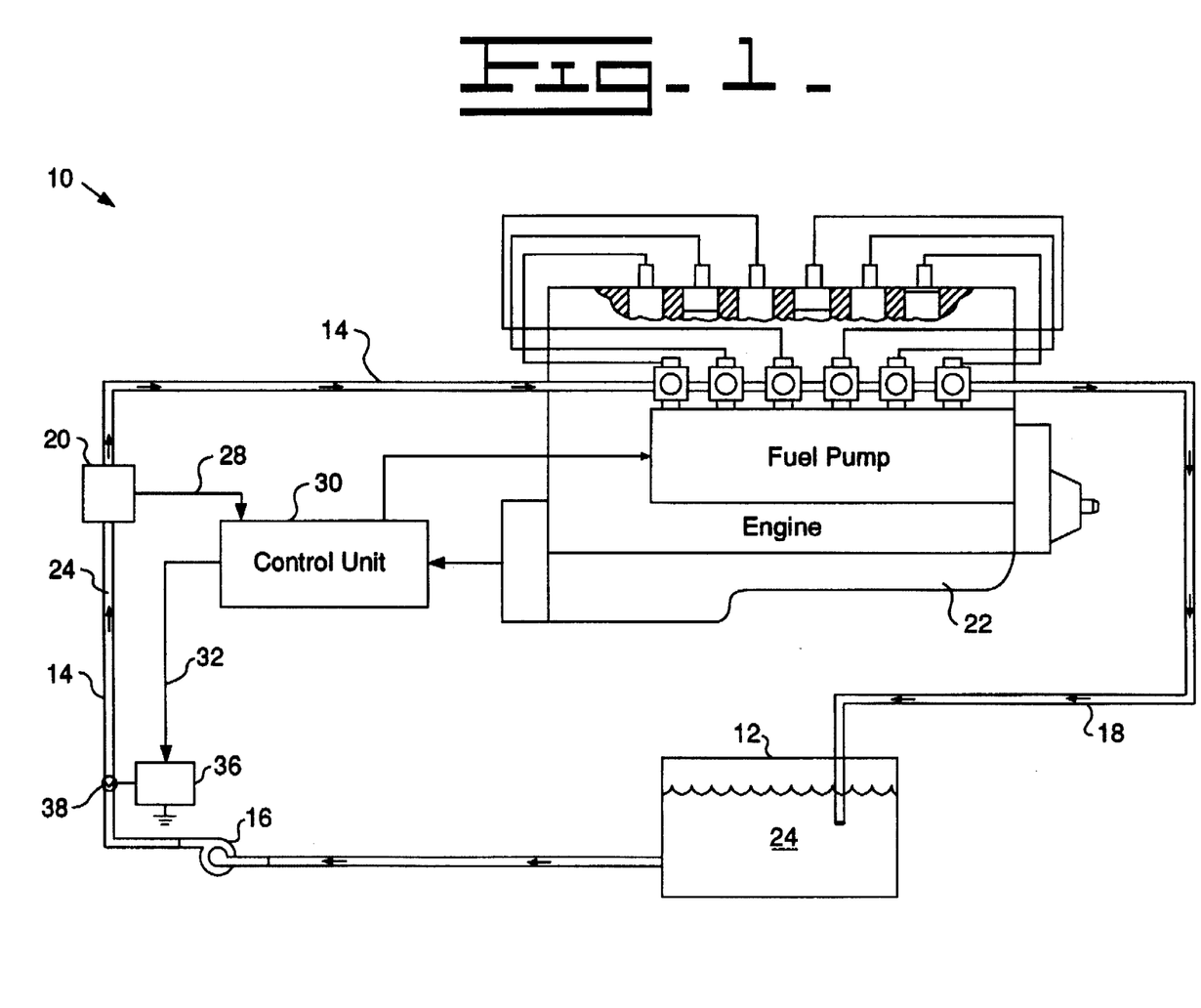
FIG. 1 is a schematic representation of the fuel identification system for an internal combustion engine adapted for using an aqueous fuel emulsion in accordance with the present invention.
Figure 2:
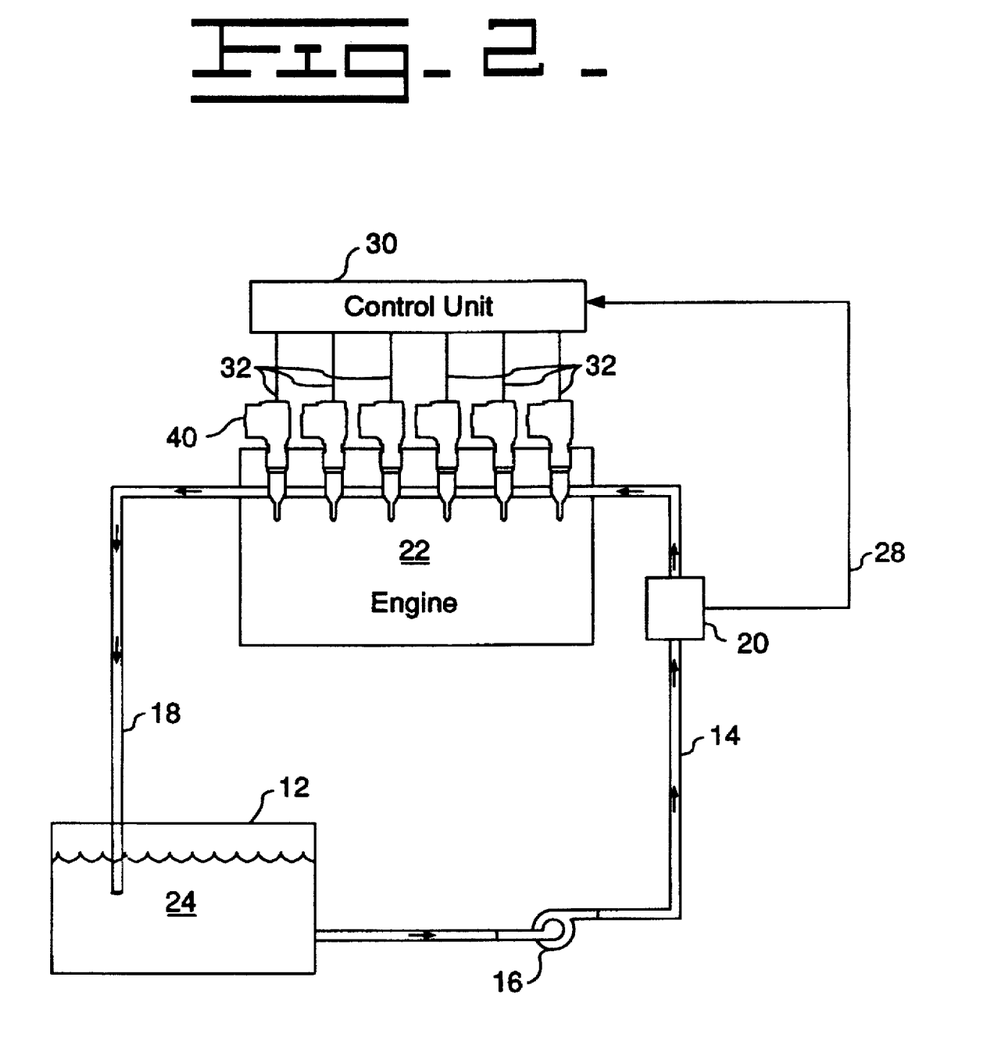
FIG. 2 is a schematic representation of an alternate embodiment of a fuel identification system for an internal combustion engine adapted to use an aqueous fuel emulsion.

Turning now to the drawings and particularly to FIGS. 1 and 2, there are shown two schematic representations of the fuel identification system for a compression ignition engine (i.e. diesel engine) adapted for using an aqueous fuel emulsion as a source of fuel. As seen therein, the fuel identification system 10 includes a fuel delivery system that includes, for example, a fuel tank 12, fuel line 14, fuel transfer pump 16, and return conduit 18. The fuel identification system 10 further includes a fuel identification sensor 20 interposed in fluid communication along the fuel line 14 between the fuel tank 12 and the engine 22, and preferably downstream of the fuel transfer pump 16. The fuel identification sensor 20 is adapted to detect selected fuel characteristics of the fuel 24 being transported within fuel line 14. Although illustrated along the fuel line 14, the fuel identification sensor 20 may be positioned elsewhere in the fuel delivery system.

The fuel identification sensor 20 provides a fuel type signal 28 for the purpose of identifying the fuel 24 within the fuel delivery system based on the detected fuel characteristics. The identification of the fuel 24 is preferably accomplished by using an optical sensor, an conductivity meter (or similar such electrical property sensor), or other sensing device that is adapted to sense physical properties (i.e. density, viscosity, etc.) of the fuel 24. The present fuel identification sensor 20 focuses on these fuel characteristics because the optical, electrical and physical properties of an aqueous fuel emulsion differ from the optical, electrical and physical properties of conventional fuels and the differences are such that one can readily distinguish an aqueous fuel emulsion from a convention fuel, such as diesel fuel.

Finally, the fuel identification system 10 also includes a control unit 30 coupled with the fuel identification sensor 20. The control unit 30 is adapted to receive the fuel type signal 28 and provide an output signal 32 for the purpose of disabling the engine 22 when a fuel 24 other than the aqueous fuel emulsion is identified as being present within the fuel delivery system. Preferably, the engine 22 is disabled by restricting or otherwise limiting the fuel flow to the engine 22. Alternatively, the engine may be disabled by closing an air shut-off valve or the existing fuel shut-off valve.

In the embodiment depicted in FIG. 1, where the fuel identification sensor 20 detects a fuel 24 other than the aqueous fuel emulsion designed for the engine 22, the fuel identification system 10 shuts off the fuel solenoid 36 associated with a fuel valve 38 along the fuel line 14 limiting or restricting fuel flow to the engine 22. Alternatively, in the embodiment depicted in FIG. 2 which includes an electronically controlled engine 22, the fuel identification sensor 20 simply sends a fuel type signal 28 to the electronic controller 30 that in turn sends an output signal 32 to the unit injectors 40 that limits the maximum rack of the engine 22 or imposes some other disabling condition on the engine.

Figure 3:
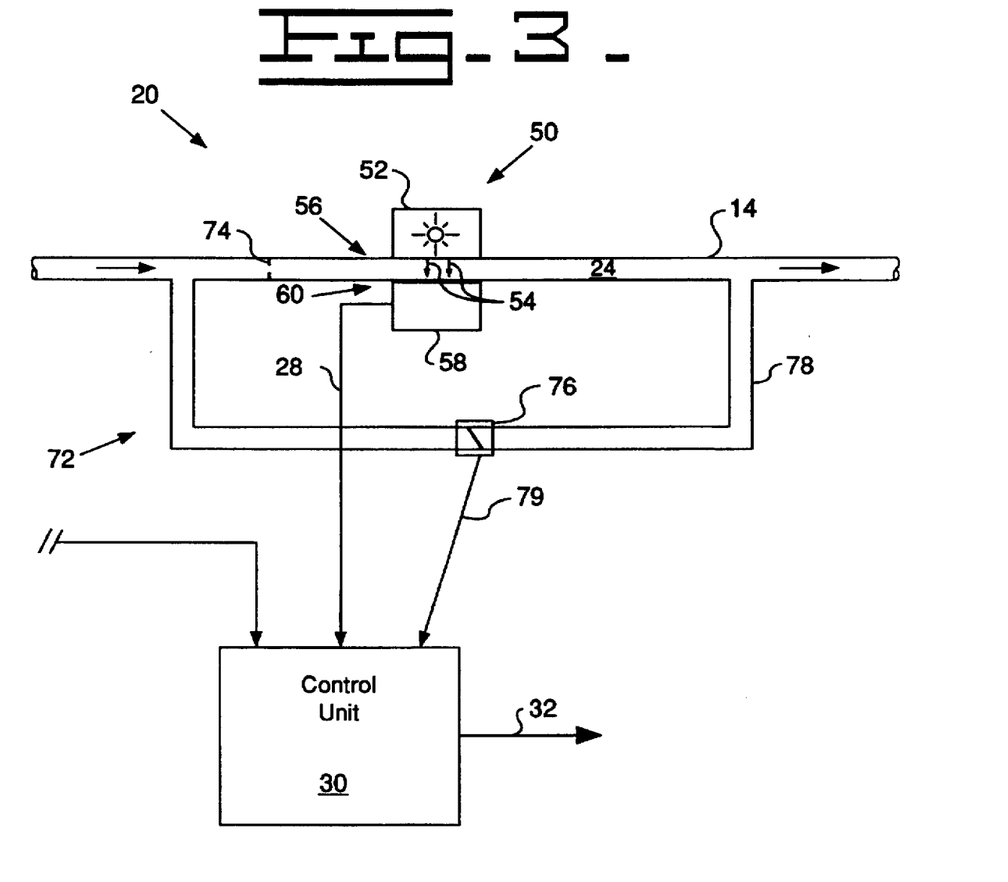
FIG. 3 is a schematic representation of an anti-tampering device including an optical based fuel identification sensor for preventing the use of selected fuels in an internal combustion engine that is adapted for using an aqueous fuel emulsion.
Figure 4:
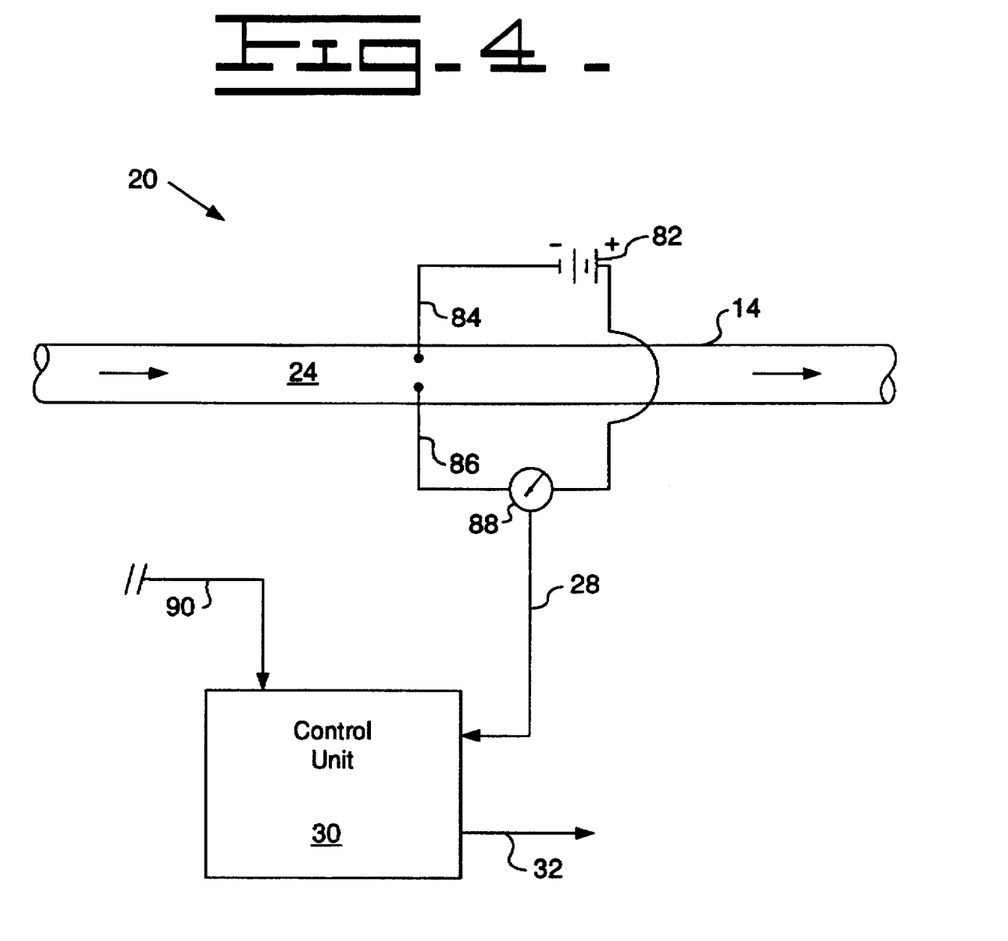
FIG. 4 is a schematic representation of an alternate embodiment of the anti-tampering device for preventing the use of selected fuels in an internal combustion engine that is adapted for using an aqueous fuel emulsion based on the electrical properties of the fuel.

Turning now to FIGS. 3 and 4, there are shown schematic representations of various embodiments of an anti-tampering device which is utilized as part of the fuel identification system 10 of FIGS. 1 and 2. The illustrated anti-tampering device includes the fuel identification sensor 20 and an associated control unit 30 and is particularly adapted for preventing the use of a selected fuels in an internal combustion engine designed only for using an aqueous fuel emulsion. As indicated above, the fuel identification sensor 20 is capable of distinguishing an aqueous fuel emulsion from a conventional fuel based on selected fuel characteristics, such as optical properties, electrical properties, or physical properties and produce a fuel type signal 28. The control unit 30 is adapted to receive the fuel type signal 28 and produce an output signal 32 that disables the engine if the fuel identification sensor 20 identifies the transported fuel 24 within the fuel line 14 as being other than the aqueous fuel emulsion.

In the embodiment illustrated in FIG. 3, the fuel identification sensor 20 consists of a optical probe or sensor 50 located near the fuel line 14 and in operative association with the fuel flowing therein. The optical sensor 50 is preferably used to determine the fuel type based on the optical characteristics of the fuel 24 in the fuel line 14. The optical characteristics, such as absorption at selected wavelengths, opacity, index of refraction, and other optical properties of an aqueous fuel emulsion often differ from the optical characteristics of diesel fuel. For example, a source of light passing through an aqueous fuel emulsion is either absorbed or reflected away whereas a diesel fuel is more transmissive in nature. In other words, many aqueous fuel emulsions do not allow light or other selected sources of radiation to simply pass through the fuel without significant absorption, reflection, or dispersion whereas diesel fuel readily transmits selected wavelengths of light with much lower levels of absorption, reflection and dispersion.

The illustrated optical sensor 50 includes a source of radiation or light 52 at a selected wavelength that is adapted to impinge a beam 54 on the fuel 24 transported within the fuel line 14 at a selected location 56. An optical receiver 58, such as a photodiode, charged couple device, or other conventional optical receiving device is disposed at a second location 60 within the fuel line 14 generally opposite the first location 56. Based on the intensity of the radiation or light received at the optical receiver 58, the type of fuel 24 being transported in the fuel line 14 can be ascertained. For example, because of the opacity of many aqueous fuel emulsions, little or no light originating from the source 52 at the first location 56 is received by the optical receiver 58 position at a second location 60 opposite thereto. For purposes of this application, opacity is defined to be the capacity of a substance to obstruct, by absorption or reflection, the transmission of light or other forms of radiant energy. Conversely, where the fuel is a conventional diesel fuel, most of the light or radiation originating from the source 52 at the first location 56 is received by the optical receiver 58 positioned at the second location 60. The optical receiver 28 generates a signal 28 corresponding to the intensity of the light received by optical receiver 58 which is generally indicative of whether the fuel 24 is an aqueous fuel emulsion or not. In particular, the fuel identification signal 28 is forwarded to the control unit 30 which compares the received intensity against a predetermined optical threshold value associated with the aqueous fuel emulsion and stored in the control unit 30. If the intensity of the light received by the optical receiver 58 and embodied in the fuel identification signal 28 is less than the predetermined optical threshold value associated with the aqueous fuel emulsion, the fuel 24 in the fuel line 14 proximate the optical sensor 50 is a permitted fuel. If, however, the intensity of the light received by the optical receiver 58 and embodied in the fuel identification signal 28 is equal to or greater than the predetermined optical threshold value, the fuel 24 in the fuel line 14 is deemed to be improper or invalid and the control unit 30 produces an output signal 32 that disables the engine, preferably by limiting the fuel flow to the engine.

FIG. 3 also depicts an embodiment of a countercheck detector 70 that is intended to ensure the fuel identification sensor 20 is not tricked by an unethical operator. In the illustrated embodiment, a flow measurement device 72 disposed proximate the fuel identification sensor 20 is used to ensure that the pressure drop across the fuel identification sensor 20 is above some predetermined threshold level. In the illustrated embodiment, the flow measurement device 72 consists of an orifice 74 located in the fuel line 14 upstream of the fuel identification sensor 20, a pressure transducer 76 or sensor located in a bypass conduit 78. If the pressure drop across the fuel identification sensor 20 is below the predetermined threshold level, a countercheck signal 79 is forwarded to the control unit 30 to limit the fuel flow to the engine or otherwise disable the engine because the fuel flow may have been manipulated or altered.

An alternate form of the anti-tampering device, as depicted in FIG. 4, uses a conductivity meter as the fuel identity sensor 20. As with the above-described embodiments, the fuel identification sensor 20 is capable of distinguishing an aqueous fuel emulsion from a conventional fuel based on selected fuel characteristics and produce a corresponding fuel type signal 28. In this embodiment, the selected fuel characteristic is the electrical properties of the fuel because it has been realized that the electrical properties of aqueous fuel emulsions often differ from the electrical properties of diesel fuel. For example, the conductivity of an aqueous fuel emulsion is different (i.e. the conductivity is higher and resistivity is lower) than that of diesel fuel.

The fuel identification sensor 20 illustrated in FIG. 4, includes a very low voltage source 82 oppositely coupled to a pair of leads 84 and 86 terminating in the fuel line 14 proximate to each other. The illustrated fuel identification sensor 20 also includes an ammeter 88 adapted to measure the electrical current passing through the circuit. The ammeter 88 generates a fuel identification signal 28 that is forwarded to a control unit 30. The control unit 30 illustrated in FIG. 4, is adapted to receive the fuel identification signal 28 from the ammeter 88 together with other related engine operating parameters 90 and produce an output signal 32 that disables the engine if the fuel 24 identified within the fuel line 14 is a fuel other than the proper aqueous fuel emulsion.

More specifically, the control unit 30 compares the electrical current measured by the ammeter 88 against some empirically determined threshold value associated with the aqueous fuel emulsion and resident in read-only memory (ROM) of the control unit 30. If the electrical current measured by the ammeter 88 and embodied in the fuel identification signal 28 is equal to or above the threshold value associated with the aqueous fuel emulsion, the fuel 24 in the fuel line 14 proximate the leads 84 and 86 is a permitted fuel. If, however, the electrical current measured by the ammeter 88 and embodied in the fuel identification signal 28 is less the threshold value associated with the aqueous fuel emulsion, the fuel 24 in the fuel line 14 proximate the leads 84 and 86 is deemed to be improper and the control unit 30 produces an output signal 32 that, as described above, disables the engine.

Figure 5:
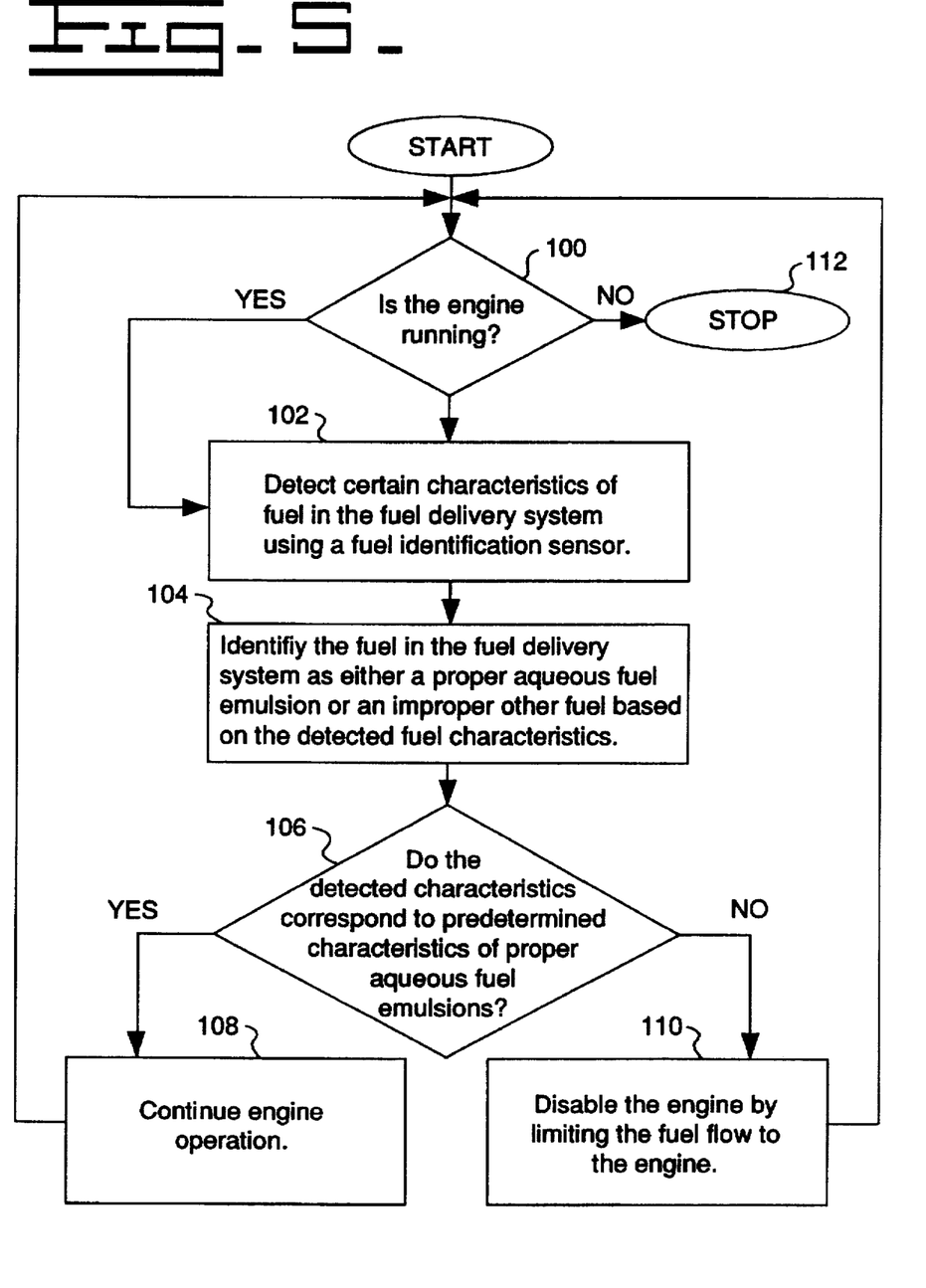
FIG. 5 is a block diagram generally depicting the preferred method for preventing the use of improper fuels in an internal combustion engine designed to use an aqueous fuel emulsion.

Turning now to FIG. 5, there is shown a block diagram generally depicting the preferred method for preventing the use of other fuels in an internal combustion engine adapted to use an aqueous fuel emulsion. As seen therein, the preferred method is active only after the engine is started. If the engine is running, (YES branch of block 100) the disclosed process includes the first step of detecting selected characteristics of a fuel in a fuel line of the diesel engine using a fuel identification sensor, essentially as described above (block 102). The detected fuel characteristics may be optical based fuel characteristics, electrical properties of the fuel, or even physical properties, such as density or viscosity of the fuel. The next step involves identifying the fuel in the fuel delivery system as either a proper aqueous fuel emulsion or an improper other fuel based on the detected fuel characteristics determined by the fuel identification sensor (block 104). The step of identifying the fuel preferably includes identifying the fuel as a proper aqueous fuel emulsion if the detected characteristics correspond to some predetermined characteristics of permitted aqueous fuel emulsions. Otherwise the fuel is identified as one of the improper fuels if the detected characteristics do not correspond to the predetermined characteristics (block 106). Where the fuel is identified as a proper aqueous fuel emulsion (YES branch of block 106), the engine operation continues uninterrupted (block 108). However, if the identified fuel is not among the permitted aqueous fuel emulsions and therefore is one of the other improper fuels (NO branch of block 106), then the engine control unit disables the engine by restricting or otherwise limiting the fuel flow to the engine (block 110). The fuel identification process continues at a prescribed frequency while the engine is running and terminates (block 112) as the engine is disabled.

The above-identified method and system for the identification of fuel in an engine can be utilized alone or in conjunction with other fuel system controlling techniques. Moreover, each of the specific steps involved in the preferred process, described herein, and each of the components in the preferred systems are easily modified or tailored to meet the peculiar design and operational requirements of the particular engine and the anticipated operating environment in which the engine is used.

For example, there are numerous other forms of suitable fuel identification sensors capable of detecting the differing physical properties, including such properties as viscosity or density, between an aqueous fuel emulsion and a conventional diesel fuel. Moreover, there are numerous measurement techniques adapted for sensing the physical, optical and electrical properties of fuels, all of which are contemplated for inclusion within the described system and methods.

From the foregoing, it should be appreciated that the present invention thus provides a method and system for the identification of the fuel within a fuel delivery system based on the difference in optical properties, electrical properties or other physical characteristics between an aqueous fuel emulsion and a conventional fuel. While the invention herein disclosed has been described by means of specific embodiments and processes associated therewith, numerous modifications and variations can be made thereto by those skilled in the art without departing from the scope of the invention as set forth in the claims or sacrificing all its material advantages.

What is claimed is:

1. An anti-tampering device for preventing the use of selected fuels in an internal combustion engine adapted to use an aqueous fuel emulsion, said anti-tampering device comprising:
   a fuel identification sensor adapted to detect selected characteristics of the fuel in a fuel delivery system of said engine;
   a control unit responsive to said fuel identification sensor and adapted to differentiate between said aqueous fuel emulsion and fuels other than said aqueous fuel emulsion and produce a signal that disables said engine when said fuel identification sensor identifies said fuel as being other than said aqueous fuel emulsion.

2. The anti-tampering device of claim 1 wherein said fuel identification sensor is an optical sensor adapted to detect optical properties of said fuel in said fuel delivery system of said engine.

3. The anti-tampering device of claim 1 wherein said fuel identification sensor is a device adapted to detect selected electrical properties of said fuel in said fuel delivery system of said engine.

4. The anti-tampering device of claim 1 wherein said fuel identification sensor is a device adapted to detect selected physical properties of said fuel in said fuel delivery system of said engine.

5. The anti-tampering device of claim 1 further comprising a countercheck detector operatively coupled to said fuel identification sensor and adapted to indicate if said fuel identification sensor has been altered or otherwise disabled.

6. The anti-tampering device of claim 5 wherein said countercheck detector includes a fuel flow measurement device operatively coupled to said fuel identification sensor and adapted to indicate if said fuel flow proximate said fuel identification sensor has been diverted.

7. A fuel identification system for preventing the use of selected fuels in an internal combustion engine adapted to use an aqueous fuel emulsion, said fuel identification system comprising:
   a fuel delivery system for said engine, said fuel delivery system including a fuel tank and a fuel line in fluid communication with said fuel tank for supplying fuel to said engine;
   a fuel identification sensor disposed in operative association with said fuel delivery system and adapted to detect selected characteristics of a fuel in said fuel delivery system;
   a control unit responsive to said fuel identification sensor and adapted to differentiate between said aqueous fuel emulsion and other fuels to produce a signal that disables said engine when said other fuels are identified as being present within said fuel delivery system.

8. The fuel identification system of claim 7 wherein said engine includes one or more electronically controlled fuel injectors and said signal from said control unit is adapted to limit the quantity of fuel injected by said fuel injectors into the engine cylinders.

9. The fuel identification system of claim 7 wherein said engine includes a fuel valve disposed in said fuel line and said signal from said control unit is adapted to control the fuel valve thereby restricting fuel flow to the engine.

10. The fuel identification system of claim 7 wherein said fuel identification sensor is an optical sensor adapted to detect optical properties of said fuel in said fuel delivery system of said engine.

11. The fuel identification system of claim 7 wherein said fuel identification sensor is a device adapted to detect selected electrical properties of said fuel in said fuel delivery system of said engine.

12. The fuel identification system of claim 7 wherein said fuel identification sensor is a device adapted to detect selected physical properties of said fuel in said fuel delivery system of said engine.

13. The fuel identification system of claim 7 further comprising a countercheck detector operatively coupled to said fuel identification sensor and adapted to indicate if said fuel identification sensor has been altered or otherwise disabled.

14. The fuel identification system of claim 13 wherein said countercheck detector includes a fuel flow measurement device operatively coupled to said fuel identification sensor and adapted to indicate if said fuel flow proximate said fuel identification sensor has been diverted.

15. The fuel identification system of claim 7 wherein said fuel identification sensor is disposed along said fuel line of said engine.

16. A method for preventing the use of other fuels in an internal combustion engine adapted to use an aqueous fuel emulsion, the method comprising the steps of:

detecting selected characteristics of a fuel in a fuel delivery system of said engine;

identifying said fuel in said fuel delivery system based on said detected characteristics;

disabling said engine when one of said other fuels are identified as being present within said fuel delivery system.

17. The method of claim 16 wherein the step of identifying said fuel in said fuel delivery system further includes identifying said fuel as an aqueous fuel emulsion if said detected characteristics correspond to predetermined characteristics and identifying said fuel as one of said other fuels if said detected characteristics do not correspond to said predetermined characteristics.

18. The method of claim 16 wherein the step of identifying said fuel in said fuel delivery system further includes identifying said fuel as one of said other fuels if said detected characteristics correspond to predetermined characteristics.

19. The method of claim 16 wherein the step of detecting selected characteristics of said fuel further comprises detecting selected optical properties of said fuel.

20. The method of claim 16 wherein the step of detecting selected characteristics of said fuel further comprises detecting selected electrical properties of said fuel.

21. The method of claim 16 wherein the step of detecting selected characteristics of said fuel further comprises detecting selected physical properties of said fuel.

22. The method of claim 16 further comprising the step of detecting evidence of tampering with said fuel delivery system and disabling said engine when evidence of tampering is detected.

23. The method of claim 22 wherein the step of detecting evidence of tampering further comprises monitoring the fuel flow in said fuel delivery system to determine whether the fuel flow has been altered.

24. The method of claim 16 wherein the step of disabling said engine further comprises the step of curtailing the quantity of fuel injected by said fuel injectors into the engine cylinders.

25. The method of claim 16 wherein the step of disabling said engine further comprises the step of shutting off a fuel solenoid operatively associated with a valve disposed in said fuel line thereby stopping fuel flow to the engine.

* * * * *